United States Patent
Thorne, Jr. et al.

(10) Patent No.: US 8,485,356 B2
(45) Date of Patent: Jul. 16, 2013

(54) METHODS FOR EXPOSING AND USING A SWAB

(75) Inventors: Gale H. Thorne, Jr., Bountiful, UT (US); Kendall P. Thorne, Layton, UT (US)

(73) Assignee: Intra Vena, LLC, Bountiful, UT (US)

( * ) Notice: Subject to any disclaimer, the term of this patent is extended or adjusted under 35 U.S.C. 154(b) by 112 days.

(21) Appl. No.: 13/200,207

(22) Filed: Sep. 21, 2011

(65) Prior Publication Data

US 2012/0012631 A1 Jan. 19, 2012

Related U.S. Application Data

(63) Continuation-in-part of application No. 12/925,122, filed on Oct. 14, 2010, which is a continuation-in-part of application No. 12/460,470, filed on Jul. 20, 2009, now abandoned, which is a continuation-in-part of application No. 12/319,326, filed on Jan. 6, 2009, now abandoned, which is a continuation-in-part of application No. 12/313,013, filed on Nov. 14, 2008, now abandoned, which is a continuation-in-part of application No. 12/080,185, filed on Apr. 1, 2008, now abandoned, which is a continuation-in-part of application No. 12/012,837, filed on Feb. 6, 2008, now Pat. No. 7,785,312.

(51) Int. Cl.
*B65D 83/10* (2006.01)
*B65D 81/24* (2006.01)
*A61M 35/00* (2006.01)

(52) U.S. Cl.
USPC ........... 206/361; 206/210; 383/205; 383/210; 604/1; 604/3

(58) Field of Classification Search
USPC .... 206/209, 210, 361; 383/205–210; 604/1–3
See application file for complete search history.

(56) References Cited

U.S. PATENT DOCUMENTS

| | | | | | |
|---|---|---|---|---|---|
| 3,199,671 | A | * | 8/1965 | Davy | 383/205 |
| 3,282,114 | A | * | 11/1966 | Pell | 206/361 |
| 3,768,725 | A | * | 10/1973 | Pilaro | 383/210 |
| 5,378,226 | A | * | 1/1995 | Hanifl et al. | 604/3 |
| 5,411,202 | A | * | 5/1995 | Fenini | 383/205 |
| 5,704,906 | A | | 1/1998 | Fox | |
| 5,996,780 | A | * | 12/1999 | Gurrera | 206/209 |
| 6,488,646 | B1 | * | 12/2002 | Zygmont | 604/1 |
| 6,494,856 | B1 | * | 12/2002 | Zygmont | 604/1 |
| 8,109,387 | B2 | * | 2/2012 | Sogaro | 206/361 |
| 8,216,171 | B2 | * | 7/2012 | Kamen et al. | 604/1 |
| 2004/0099543 | A1 | * | 5/2004 | Tsaur | 206/210 |
| 2005/0111765 | A1 | * | 5/2005 | Beaulieu | 383/205 |
| 2008/0119776 | A1 | * | 5/2008 | Wu | 604/1 |

* cited by examiner

*Primary Examiner* — Bryon Gehman
(74) *Attorney, Agent, or Firm* — Gale H. Thorne

(57) ABSTRACT

A method for remotely applying a force to a tether affixed to a sterilizing swab package to open the package for use of a swab disposed therein. The method may be applied to sterilizing a septum of a vial disposed within a bag.

6 Claims, 3 Drawing Sheets

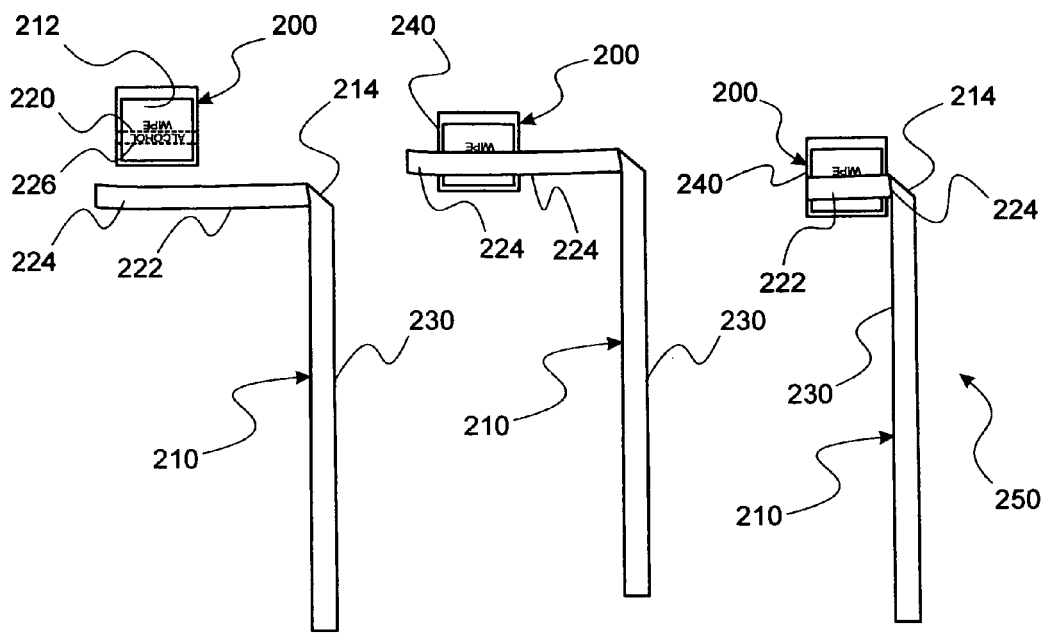
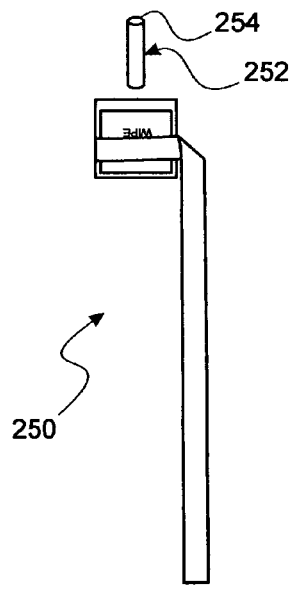 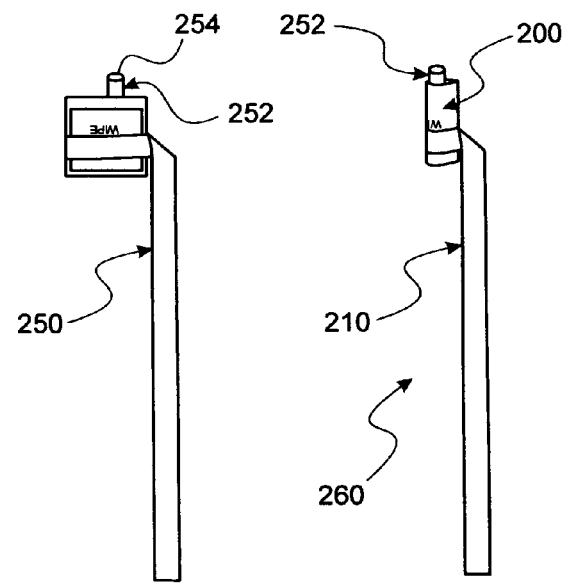
FIGURE 1  FIGURE 2  FIGURE 3
FIGURE 4  FIGURE 5  FIGURE 6

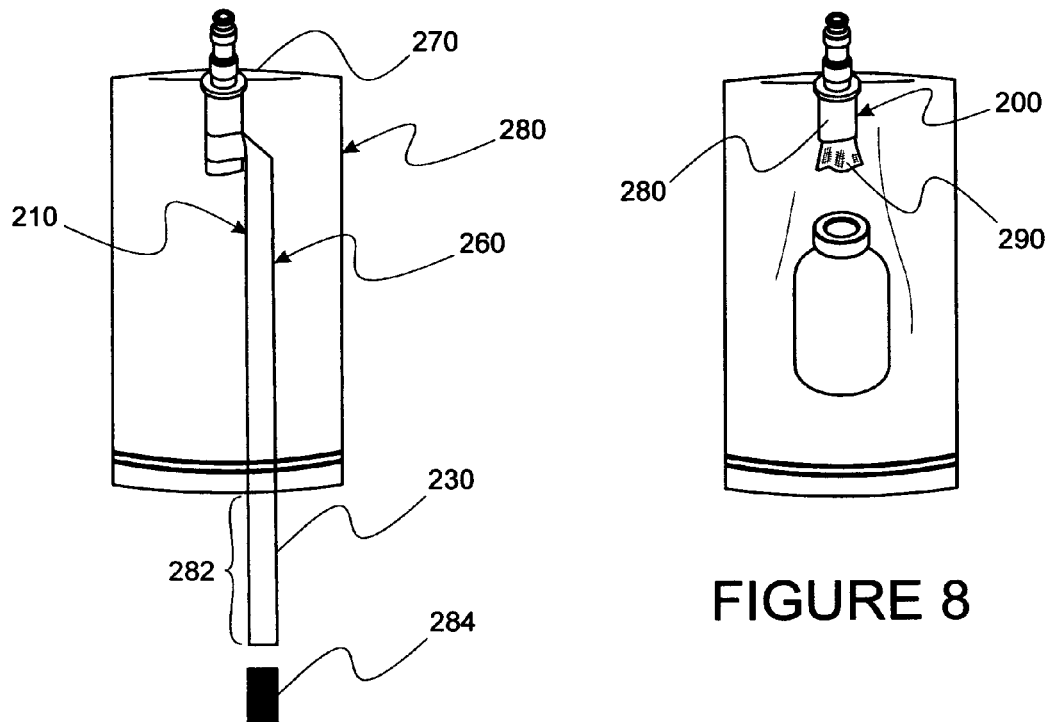
FIGURE 7
FIGURE 8
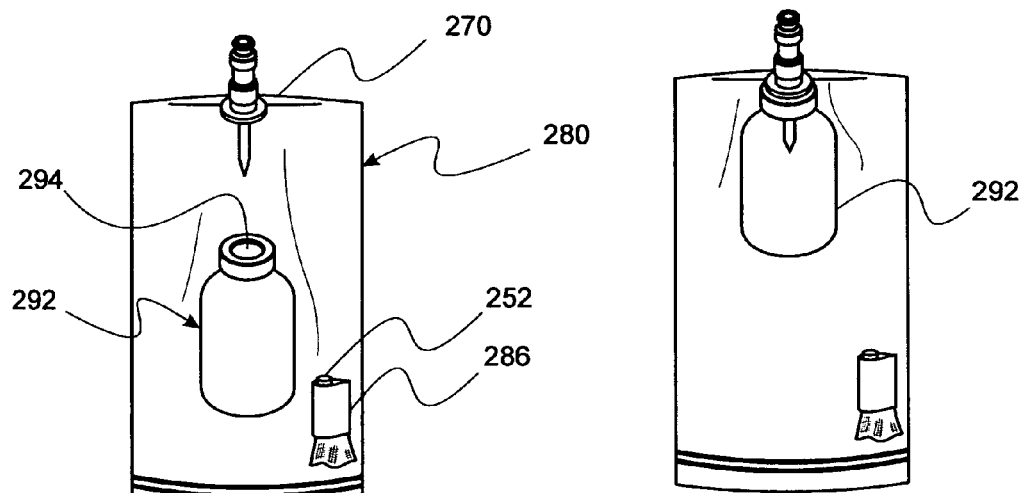
FIGURE 11
FIGURE 12

METHODS FOR EXPOSING AND USING A SWAB

CONTINUATION-IN-PART

This application for patent is a Continuation-in-Part of U.S. patent application Ser. No. 12/925,122 filed Oct. 14, 2010 which is a Continuation-in-Part of U.S. patent application Ser. No. 12/460,470, filed Jul. 20, 2009, now abandoned, which is a Continuation-in-Part of U.S. patent application Ser. No. 12/319,326 filed Jan. 6, 2009, now abandoned, which is a Continuation-in-Part of U.S. patent application Ser. No. 12/313,013, filed Nov. 14, 2008, now abandoned, which is a Continuation-in-Part of U.S. Ser. No. 12/080,185, filed, Apr. 1, 2008, now abandoned, which is a Continuation-in-Part of U.S. patent application Ser. No. 12/012,837 filed Feb. 6, 2008, now allowed as U.S. Pat. No. 7,785,312, the contents of which are made part of this application by reference.

FIELD OF INVENTION

This invention generally relates to methods for making and using medical convenience kits and, more specifically, for making convenience kits which have a specific purpose of enclosing a vial to provide a closed system for transferring solutions from vials to IV dispensing systems used in patient drug delivery and especially for drug delivery using medicines which present a hazard if exposed to an open environment. More specifically, methods associated with this invention are related to opening, accessing and using a sterilizing swab within a plastic bag.

BACKGROUND AND DESCRIPTION OF RELATED ART

This invention is directly related to disclosure contained in U.S. patent application Ser. No. 12/925,122 (Thorne 122) from which this application continues in part and which is made part of this application by reference. As disclosed and seen in FIGS. 15A-D of Thorne 122, an alcohol wipe 190 is commonly used to swab a septum of a vial prior to spiking vial, usually for procedures associated with drawing a dose of medicine from a vial. Prior art effort leading up to swabbing is generally laborious and subject to occasional blunders associated with handling a swabbing pad within a plastic bag.

As seen in FIG. 15A of Thorne 122, preparation for use of an alcohol swab involves removing the swab from a package in which it is delivered. This usually involves tearing open the package and removing a pad which is identified as swab 190 in Thorne 122. When the bag is inverted for displacing a vial 192 into the bag, the swab 190 must be physically restrained from falling out of the bag, as seen in FIG. 15B. As seen in FIG. 15C, further restraint may be necessary when removing a cap 194 from the vial. Once the cap is removed to reveal a pierceable septum of the vial, swab 190 must be accessed and displaced to swab the septum as seen in FIG. 15D. Manual steps associated with such activity are labor intensive and time consuming when dealt with in a pharmacy laboratory dedicated to efficacy in drug acquisition from vials.

BRIEF SUMMARY AND OBJECTS OF THE INVENTION

In brief summary, this novel invention provides a basis for innovative processes employed for opening a package containing a sterilizing pad (e.g. an alcohol swab) using an elongated pull strip. As an example, the swab package may be disposed within an enclosing and surrounding plastic bag in which all contents have been sterilized. The pull strip may have a free end disposed outside the bag and be pulled to tear open the package without contaminating contents of the bag. Thus, the instant invention provides for an improved mode for efficiently exposing a pad or swab within a bag. Further, the instant invention provides for a construction which facilitates swabbing (e.g. swabbing an exposed vial septum within a bag).

Thus, the instant invention involves a method for accessing a swab pad from a conventional swab package having tearable exterior material. The swab pad, is most commonly saturated with alcohol, although other sterilizing materials could be used within the scope of the invention to wipe or swab and, thereby, sterilize a surface. Historically, the swab pad is accessed by tearing the swab package apart and displacing the swab pad from the package for use.

As a part of the method of the instant invention, a pull strip of predetermined length is provided. The pull strip should be of sufficient length to completely girdle the package and still have a free end of sufficient length for grasping and pulling digitally. The pull strip is adhesively affixed about the swab package along a prospective tear line such that the package, when torn along that line, is separated into two parts.

As an example, the pull strip may be made from TYVEK® (a material which can survive a pull of sufficient force to tear the package material, or a plastic tie material, both of which are currently available commercially.

Though it may be accomplished in other ways within the scope of the instant invention, it is preferred to apply adhesive (e.g. low temperature hot glue) to the pull strip and thereby affix the pull strip circumferentially about the package such that a tear line is defined by adhesive attachment of pull strip to exterior material of the package. The tear line is defined to provide complete separation of the package when employed. For the pull strip to be effectively attached, an end of the pull strip associated with the tear line should be securely affixed to the free portion of the pull strip.

With the pull strip so adhesively affixed, the package is opened by firmly holding a portion of the package away from the pull strip (and direction of pull) and pulling upon the free end of the pull strip. Such pulling tears the package along the adhesive bond between the package and pull strip. By defining the pull strip to be affixed to the package along a medial line associated with the displacement of the swab pad in the package, the package is parted to expose a segment of the enclosed swab pad. So exposed, the swab pad is available for use in providing an aseptic surface treatment.

One area of application is when a swab pad is used for sterilizing a septum of a vial as disclosed in Thorne 122. In such a case, the bag exterior away from the tear line and part which is separated by pulling on the pull strip may be affixed to a spike cover. By doing so, when the package is separated to expose a segment of the swab pad, the spike cover may be used as a handle and the swab utilized as a brush to wipe the septum. Of course, any member, attachable to the package, may be affixed to the package to act as a handle when an item like the spike cover is unavailable.

Accordingly, it is a primary object to provide methods for affixing a pull strip to an alcohol swab package for remotely tearing the package apart to thereby provide a separated part affixed to the pull strip while the rest of the package provides an exposed swab pad which then may be used for an aseptic surface treatment.

It is an important object to provide a method for remotely accessing a swab pad initially contained in a tear-able package which is disposed within a plastic bag of sterilized items.

These and other objects and features of the present invention will be apparent from the detailed description taken with reference to accompanying drawings.

BRIEF DESCRIPTION OF THE DRAWINGS

FIG. 1 is an exploded view of an exemplary conventional alcohol swab package and a dissociated folded pull strip.

FIG. 2 is a frontal elevation of the alcohol swab package seen in FIG. 1 with the pull strip disposed over an area of adhesive attachment and tear line of the swab package.

FIG. 3 is a frontal elevation of the alcohol swab package seen in FIG. 2 with the pull strip adhesively affixed to the swab package to provide a tear-able assembly.

FIG. 4 is an exploded view of the tear-able assembly seen in FIG. 3 and an associated spike cover.

FIG. 5 is a frontal elevation of the tear-able assembly seen in FIG. 4 with the spike cover disposed for attachment to the assembly.

FIG. 6 is a frontal elevation of the combination seen in FIG. 5 with the swab package wrapped about the spike cover.

FIG. 7 is a frontal elevation of the combination seen in FIG. 6 with the spike cover affixed to a vial adapter spike disposed within a plastic bag.

FIG. 8 is a frontal elevation of the combination disposed as seen in FIG. 7 with a pull strip and portion of the package removed.

FIG. 11 is a perspective of the items seen in FIG. 10 with the vial spike cover and associated opened spike package assembly separated from the vial adapter.

FIG. 12 is a perspective of the items seen in FIG. 11 with the vial spiked.

DETAILED DESCRIPTION OF THE ILLUSTRATED EMBODIMENTS

Figure 9:
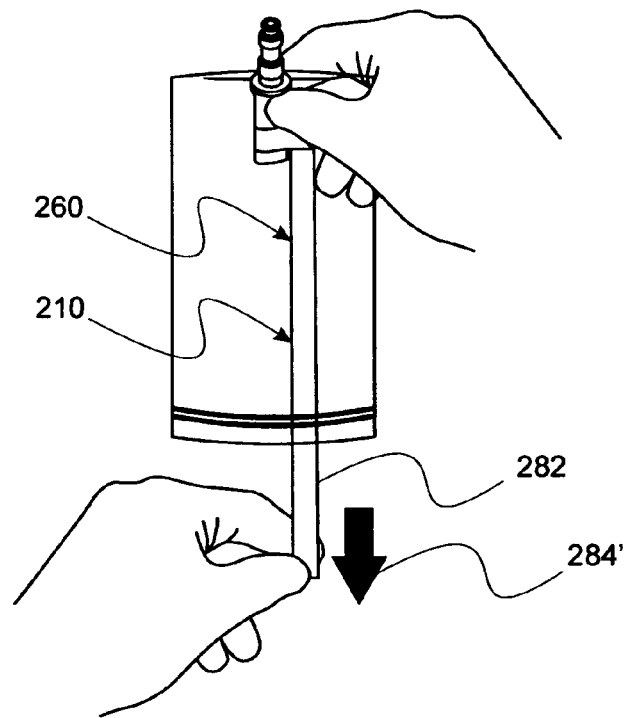
FIG. 9 is a perspective of the items seen in FIG. 7 showing hand positions for pulling the pull strip to tear open the swab package.

Reference is now made to the embodiments illustrated in FIGS. 1-12 wherein like numerals are used to designate like parts throughout. For parts which are similar but not the same as parts originally specified with a given number, a prime of the original numbers is used. It is important that all parts selected for use in convenience kits associated with the instant invention, be able to be sterilized, for example, by such methods as gamma radiation.

Reference is now made to FIG. 1 wherein an alcohol swab package 200 and an elongated pull strip 210 are seen as provided for assembly. Swab package 200 represents products which are available generally from a raft of commercial sources today. Typical of all such products is a tear-able exterior material 212. Contained within the package is a pad (not shown in FIG. 1) which is saturated with a sterilizing agent (e.g. alcohol). As well as being tear-able, exterior material 212 is designed to be substantially impervious to alcohol or other sterilizing agent contained therein.

Pull strip 210 is seen to be folded along a line 214 in FIG. 1 to permit application of force orthogonal to a tear line 220 of package 200. An elongated segment 222 of pull strip 210 extends away from line 214 to an end section 224. A sufficient length for segment 222 is provided to completely wrap about package 200 along line 220 and a like line (not shown) on the opposite side of package 200 and further to permit end segment 224 to overlap line 214. While it is preferable to apply adhesive to segment 222 of pull strip 210 when affixing pull strip 210 to package 200, a second line 226 defines a width of adhesive applied to package 200 via pull strip 210 (i.e. an area on package 200 between lines 220 and 226. A similar area of adhesion (not shown) is utilized on the backside of package 200. Note an elongated portion 230 of pull strip 210 extends away from package 200.

After applying adhesive to the underside (not shown) of segment 222, pull strip 210 is displaced in contact with package 200, as seen in FIG. 2. Segment 222 is folded about an edge 240 of package 200 and extended to adhesively engage that portion of pull strip 210 about line 214 with end section 224 to form a completed subassembly 250.

For an application involving a vial adapter spike (as disclosed in Thorne 122), a spike cover 252 seen in FIG. 4 (referenced as cover 16 in Thorne 122) is provided for generally protecting a vial spike before use. An open end 254 of cover 252 is disposed as seen in FIG. 5 for further assembly about a vial spike. Subassembly 250 is preferably affixed to cover 252 between line 220 and open end 254. Also preferably, package 200 (and segment 222) is wrapped about cover 252 to form a handle shape, as seen in FIG. 6, ultimately forming assembly 260.

In preparation for use in a plastic bag application, assembly 260 is affixed to a vial spike adapter 270 (with cover 252 disposed within a plastic bag 280, as seen in FIG. 7. Note, that a length 282 of portion 230 of pull strip 210 extends out of bag 280 for access and use as disclosed in detail hereafter. By applying a pull force to pull strip 210 in direction of arrow 284, with proper restraint of package 200, a portion of package 200 may be torn away. Thus, a remaining portion 286 of package 200, seen in FIG. 8, is yet disposed about cover 252 (not seen in FIG. 8) with a portion of a swab pad 290 exposed.

Figure 10:
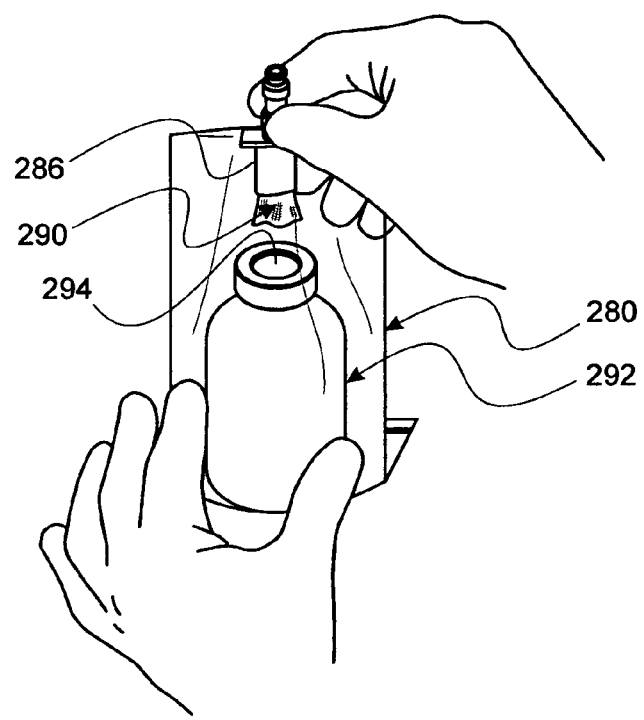
FIG. 10 is a perspective of the items seen in FIG. 8 with a vial, with septum cover removed, disposed in the bag showing suggested hand positions for swabbing a septum of the vial.

Note, as seen in FIG. 10, vial 292, with a cap (not shown) removed prior, inserted into bag 280, has an exposed septum 294. With remaining portion 286 so affixed to cover 252 (not seen in FIG. 10), septum 294 is readily swabbed as by painting with swab pad 290 acting as a brush. Cover 252 and remaining portion 286 provides function of a handle for facile swabbing of septum 294.

Once sterilizing of septum 294 is complete, cover 252 and remaining portion 286 are removed from vial adapter 270 as seen in FIG. 11. Septum 294 of vial 282 is then spiked as seen in FIG. 12.

Elements of the invention may be embodied in other specific forms and methods without departing from the spirit or essential characteristics thereof. The present methods are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A method for accessing a swab pad from a conventional swab package, disposed within a vial enclosing plastic bag, comprising the steps of:
   providing the vial enclosing plastic bag which is used for the purpose of enclosing a medical drug vial and an associated swab package;
   providing the conventional swab package from which a swab pad saturated with a sterilizing agent is at least partially uncovered for swabbing and thereby sterilizing a surface, said package comprising an exterior cover of material which confines the swab pad and sterilizing agent within the package and which is torn apart for access to the swab pad;

providing an elongated pull strip of predetermined length, said pull strip having a first end and a second end, an intermediate portion there between and having a surface which can be adhesively affixed to the exterior of the cover material, said pull strip being of sufficient length to girdle the package and extend outward from the bag when disposed therein;

wrapping the pull strip about the package along a predetermined tear line of the cover material, adhesively joining the surface of the pull strip to the cover thereat and securely affixing the first end of the pull strip to the intermediate portion of the pull strip such that a segment of said pull strip associated with the second end extends away from the package, said tear line being disposed to provide access to at least a part of the swab pad when a portion of the package is torn away from a remaining portion of the package along the tear line and displaced from the remaining portion of the package;

disposing said package and associated portion of said pull strip inside said enclosing plastic bag such that the second end of said pull strip, which is remote from the swab package, is accessibly disposed outside the bag;

through the plastic of the bag, firmly grasping the package away from the tear line about that portion of the package which is to remain and pulling upon the second end of the pull strip to tear that portion of the package which is affixed to the pull strip apart from the remaining portion of the package thereby exposing that segment of the swab pad which is first disposed within the removed portion of the package without contaminating contents of said bag.

2. A method for accessing a swab pad according to claim 1 comprising a step of affixing a portion of the rest of the package about a rigid elongated member within the bag such that when the portion affixed to the pull strip is removed, a resultant construction is a brush saturated with a sterilizing agent with the elongated member acting as a handle and the rest of the package and exposed swab acting as the swabbing portion.

3. A method for accessing a swab pad according to claim 2 where in the portion affixing step comprises affixing the remaining portion of the package to a cover of a vial spike.

4. A method for accessing a swab pad according to claim 1 wherein the adhesively affixing step comprises applying hot glue to the package exterior and pull strip.

5. A method for accessing a swab pad according to claim 1 wherein the pull strip providing step comprises providing a strip made from a length of plastic tie material.

6. A method for accessing a swab pad according to claim 1 wherein the swab package providing step comprises providing a pad saturated with alcohol.

* * * * *